United States Patent

Polito

[11] 4,021,535
[45] May 3, 1977

[54] REAGENTS USED IN THE RADIOIMMUNOASSAY OF DIGOXIN

[75] Inventor: Alan J. Polito, Costa Mesa, Calif.

[73] Assignee: Beckman Instruments, Inc., Fullerton, Calif.

[22] Filed: Jan. 14, 1975

[21] Appl. No.: 540,809

[52] U.S. Cl. .................................. 424/1; 536/7; 424/182
[51] Int. Cl.² ........................................ A61K 43/00
[58] Field of Search .............. 260/210.5; 536/4, 6, 536/7; 424/1

[56] References Cited

UNITED STATES PATENTS

| | | | |
|---|---|---|---|
| 3,471,470 | 10/1969 | Heider et al. | 260/210.5 |
| 3,753,975 | 8/1973 | Kaiser et al. | 260/210.5 |
| 3,804,825 | 4/1974 | Losel et al. | 260/210.5 |

OTHER PUBLICATIONS

British Medical Bulletin, Hunter, W. M., "Prep. and Assessment of Radioactive Tracers," vol. 30, No. 1, 1974, pp. 18–23.
"¹²⁵I and ³H Radioimmunoassay Kits For Digoxin and Digitoxin," Schwart/Mann Flyer, Aug. 1973.
Fieser, et al., "Reagents for Org. Syn." Wiley and Sons, Inc., 1967, p. 1223.

Primary Examiner—Lewis Gotts
Assistant Examiner—Cary Owens
Attorney, Agent, or Firm—Knobbe, Martens, Olson, Hubbard & Bear

[57] ABSTRACT

The derivatives of digoxin useful in the radioimmunoassay of digoxin having the following formulae:

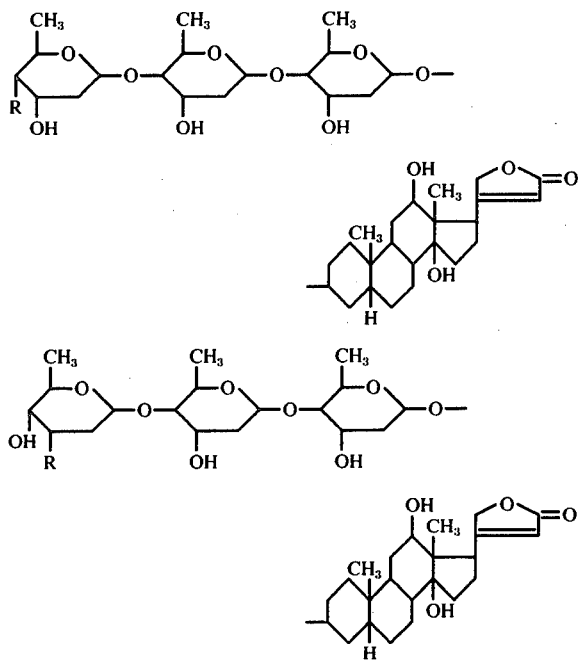

where R is a carboxylic acid ester. These derivatives are formed by the following process: (1) reacting the carboxylic acid in the presence of trifluoroacetic anhydride with a solution of digoxin in an inert, nonaqueous solvent medium, (2) adding water so as to form the above derivatives, (3) purifying the above derivatives from other constituents of the reaction mixture and (4) radio-labeling these derivatives for use as a labeled hapten in the radioimmunoassay of digoxin.

The preferred carboxylic acids are imidazoleacetic acid and p-hydroxyphenylpropionic acid. The preferred radioactive isotope is $^{125}I$.

9 Claims, No Drawings

REAGENTS USED IN THE RADIOIMMUNOASSAY OF DIGOXIN

BACKGROUND OF THE INVENTION

This invention relates to the preparation of reagents which are useful in the radioimmunoassay (RIA) of digoxin. Specifically, the present invention relates to the reagents formed by the reaction of digoxin and a carboxylic acid in the presence of trifluoroacetic anhydride and then employed in the RIA of digoxin.

Radioimmunoassay is a relatively new type of clinical analysis test. It is now being used to detect a large number of biological agents including digoxin. One of the great advantages of RIA over other clinical diagnostic procedures is the high sensitivity and specificity resulting from the nature of the antigen-antibody or hapten-antibody interactions. Because of the sensitivity, RIA can easily measure antigenic and haptenic concentrations in the ranges of micro-, nano-, and picograms. While all of the conventional principles and techniques of RIA are too extensive to discuss in this application [a good insight into them can be found in an article entitled "Radioimmunoassay" by Skelly et al., Clinical Chemistry, Vol. 19, No. 2, (1973), pp. 146–174], the test is based on the fact that radio-labeled (i.e., labeled with radioactive isotopes) antigen or hapten molecules will compete with nonlabeled antigen or hapten molecules for binding sites on an antibody. Thus, through an RIA analysis, the unknown concentration of nonlabeled antigen or hapten can be found in blood plasma, serum or urine of the patient.

With respective to digoxin, several approaches have been undertaken to radio-label digoxin in order that RIA could be performed. The first approach was to tag the molecule with tritium ($^3H$). However, tritium-labeled digoxin has a relatively low specific activity for use in RIA. And, since tritium is a beta emitter and therefore usually counted by use of a liquid scintillation counter, quantifying a specific amount of this material requires laboreous precedures.

$^{125}I$ is known as a much better isotope for radio-labeling, but it cannot be chemically bound on the digoxin molecule itself. Workers in this area have made derivatives of the digoxin molecule that accept $^{125}I$ either by adding amino acids to the whole molecule [see Wilkinson, S., Chem. Abstr., 80, 105620g (1974)] or by adding amino acids to the steroid part of digoxin [see Rutner et al., Chem. Abstr., 78, 72454j (1973). Some of these amino acids contain phenyl groups onto which $^{125}I$ can be tagged.

However, the above derivatives presented problems. They usually possess different affinities toward the antibody as compared to the natural digoxin molecule. Moreover, addition of the phenyl group contained in the amino acid would make the derivative bind to other substances besides the antibodies (e.g. proteins in the plasma or serum and the surfaces of plastic test tubes).

Therefore, it was desirable to make a derivative of digoxin having the structure as close as possible to the structure of the natural digoxin molecule, be capable of being radio-labeled by an isotope such as $^{125}I$ and possessing similar binding abilities as digoxin.

BRIEF SUMMARY OF THE PRESENT INVENTION

The present invention contemplates derivatives of digoxin having the following structural formulae:

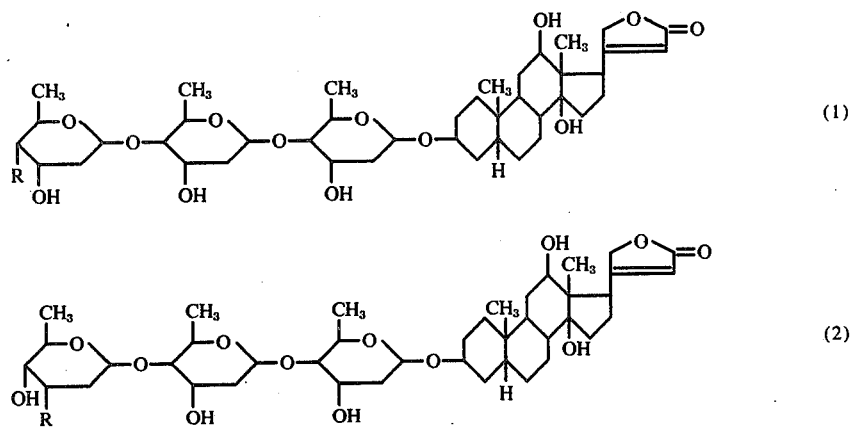

where R is a carboxylic acid ester.

These derivatives (Formulae 1 and 2) are made by (1) reacting a carboxylic acid in the presence of trifluoroacetic anhydride with a solution of digoxin in an inert, nonaqueous solvent medium, (2) adding water so as to form the above derivatives, and (3) purifying these derivatives from other constituents of the reaction mixture. These derivatives then can be radio-labeled with a radioactive isotope and used in RIA analysis of digoxin.

The major objective of the present invention is to make a radio-labeled reagent for use in RIA analysis or other protein competitive-binding analysis.

A feature of the present invention is that the present reagent has relatively similar binding properties as natural digoxin.

Other features of the present invention are that these radio-labeled reagents are very similar in structure to the natural digoxin molecule and will have the required high specific activity so that the reagent will have the required sensitivity that is needed in RIA analysis.

An advantage of the present invention is that the present reagents can be easily made without great expense or effort.

The foregoing and other objects, features and advantages of the present invention will be more readily understood upon consideration of the following detailed description.

DETAILED DESCRIPTION

Digoxin (Formula 3) is a steroid glycoside present in natural digitalis and widely used as a substitute for digitalis in hospitals and medical labs. Recently, RIA has been used to determine the precise quantity of digoxin in blood and to aid in the analysis of digoxin toxicity in patients.

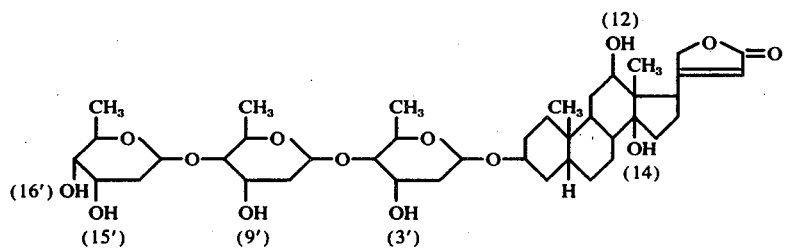

The first step in the chemical synthesis of the reagents in the present invention is reacting a carboxylic acid in the presence of trifluoroacetic anhydride with digoxin in an inert, nonaqueous solvent medium.

The digoxin which is employed herein can be obtained from any commercial source and should be in as relatively pure form as possible. Any carboxylic acid which is capable of reacting with digoxin in the presence of trifluoroacetic anhydride and also capable of being radio-labeled with a radioactive isotope can be used. The most preferred acid is imidazoleacetic acid (Formula 4 below), although p-hydroxyphenylpropionic acid (Formula 5) can also be employed.

During the first step of the present invention, there are two competing sets of the reactions. The desired and main reaction set (see Equation I) includes, first, a reaction between trifluoroacetic anhydride and the carboxylic acid to form a mixed anhydride and trifluoroacetic acid and, second, the reaction of the mixed anhydride at one of hydroxyl sites on the digoxin molecule form a carboxylic acid ester and again liberate trifluoroacetic acid as a side product (the reaction mechanism here is thought to involve the acylium R'-C$^+$=O ion).

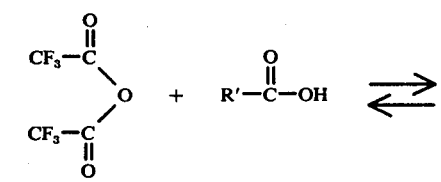

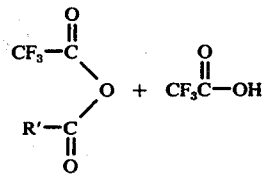

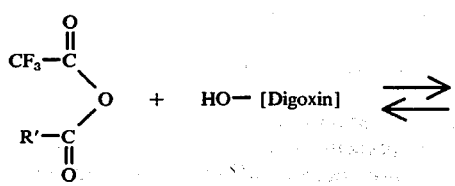

(I)

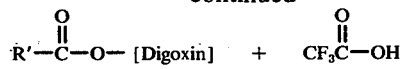

The second and minor undesired reaction (Equation II) is an acetylation reaction between the trifluoroacetic anhydride and a hydroxyl on the digoxin molecule itself to form a trifluoroacetic acid ester on the digoxin and again liberating trifluoroacetic acid.

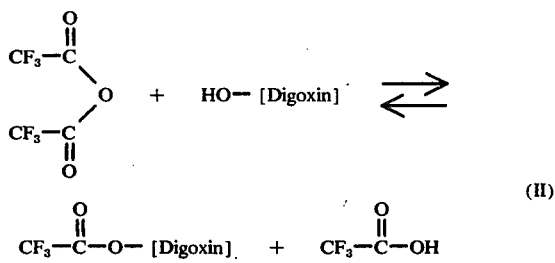

(II)

The acylation step of the first reaction through the mixed anhydride is faster than the acetylation through the trifluoroacetic anhydride (Equation II). Thus, the dominant product is the carboxylic acid ester of digoxin.

To complicate things, both sets of reactions may include reactions on any of the six hydroxyls of digoxin. See Formula 3. However, it is desirable that the esterification to a substantial degree occur at the 16'- or 15'hydroxyls so as to eliminate as much purification processing as possible. A reaction at the 12-hydroxyl on the steroid portion of digoxin is not wanted because if this hydroxyl is esterified with a carboxylic acid then resulting digoxin derivative will not bind to the antibody during the RIA.

How this desired esterificaton is accomplished can be shown by a study of the rates of reaction of the various hydroxyl groups. It is believed that the order reaction is 16'-, 12-, 15'-, 9'-, 3'-, 14-. This can be explained by the fact that the 16'-hydroxyl on digoxin is in an equatorial position and hence undergoes very little steric hindrance. Although the 15'- is located adjacent to the 16'-, the 15'-, is in an axial position instead of an equitorial position and thus will not react as readily as the 16'-. Further, it has been found that only under energenic conditions are the axial hydroxyl groups in both inner digitoses (9' and 3') esterified. Of the hydroxyls present on the steroid portion of the molecule, the 12-hydroxyl possesses a reactivity less than the 16'- but greater than the other hydroxyls on the sugar portion of the molecules. However, 14-hydroxyl is buried within the steroid backbone and thus possesses very little reactivity as compared as to the rest of the hydroxyls.

Thus, esterification conditions should be set up so that the desired 16'-ester is substantially the only one formed. This can be accomplished by using relatively mild esterification conditions such as reaction temperatures of around 35°-60° C and reaction times from about 15 to 60 minutes. Also, the molar ratio of the carboxylic acid to digoxin should be such that there is a slight excess of the acid to digoxin. However, in any event, the reaction conditions (i.e., molar ratios, reaction times and temperatures, the amount of solvent, etc.) are not critical to the present invention and would be within the skill of one having ordinary skill in the art to use conventional known reaction conditions apt to produce the above derivatives (Equation I).

It should also be noted that the mixed anhydride of Equation I may be first reacted with itself instead of reacting with digoxin. When this happens, it forms a corresponding [see Equation (III-A)]dimeric anhydride. This, in turn, may react with a hydroxyl on digoxin and thus form dimer-ester derivatives there of [see Equation (III-B)]. These dimeric esters are also contemplated as a desirable product of the present invention if they are on the 15'- or 16'-positions of digoxin.

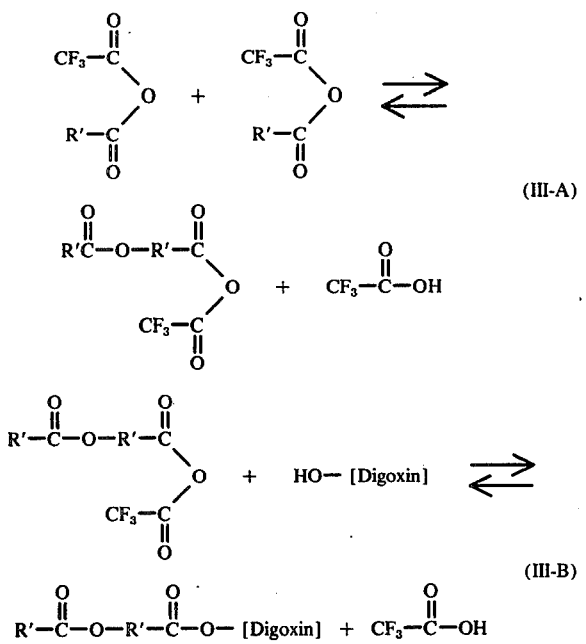

The preferred carboxylic acids for the present invention are imidazoleacetic acid [formula (4)] and p-hydroxyphenylpropionic acid [formula (5)]

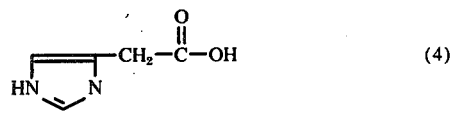

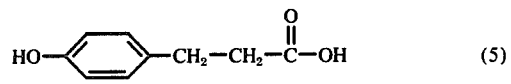

since both react readily with trifluoroacetic anhydride and possess the ability to be radio-labeled, especially with $^{125}$I.

However, any carboxylic acid having these characteristics can be used in the present invention. Imidazoleacetic acid is particularly preferred because derivatives of digoxin made from it will not nonspecifically bind to other substance besides the antibodies (e.g. proteins in the plasma or serum of blood and the surfaces of plastic test tubes). It is thought that the reduction in nonspecific binding with this derivative as compared to corresponding digoxin derivative of p-hydroxyphenylpropionic acid is due to the polar nature of the imidazole group relative to the non-polar characteristics of the phenyl group.

It is critical to the present invention that trifluoroacetic anhydride and an inert, nonaqueous solvent medium be present in the first step. Any commercial source of trifluoroacetic anhydride can be employed. The amount of trifluoroacetic anhydride should be sufficient to react with the carboxylic acid and yet given minimal reaction with digoxin. Therefore, a slight excess of trifluoroacetic anhydride over the molar amount of carboxylic acid is preferred to give maximum reaction.

The solvent medium should be inert to any reaction with the other three constituents in the first step or the water in the second step. The solvent medium should have substantially no aqueous component because water reacts with trifluoroacetic anhydride to cleave the anhydride and form trifluoroacetic acid, which in great amounts may hydrolyze the sugar portions of digoxin. The preferred inert, nonaqueous solvent medium is pyridine; however, other similarly inert nonaqueous solvents can be used such as dixoane and tetrahydrofurane. The amount of solvent should be enough so as to solubilize the mixture and allow the reaction to proceed. Like the other reaction conditions, the exact amounts of trifluoroacetic anhydride and the inert, nonaqueous solvent medium are not critical to the present invention and one having ordinary skill in the art would know how to determine optimum amounts.

Preferred mode for carrying out the reaction sequence of the first step is to:

Add the trifluoroacetic anhydride to the carboxylic acid so that the mixed anhydride is first formed, then add a solution of digoxin in an inert, nonaqueous solvent to that.

This sequence of addition of reagents allows the mixed anhydride to be formed first and thus limits the reaction of trifluoroacetic anhydride and digoxin.

The second step of this invention is to add water to the mixture after the above reactions have occurred. This step is usually carried out close to room temperature because it has been found the reaction will be uncontrollable or otherwise too strong so as to break apart the sugar portion of the digoxin molecule at high temperatures. By this procedure [see Equations (IV) and (V)] all the trifluoroacetic acid esters are cleaved and thus one is left with the desired carboxylic acid esters of digoxin and digoxin itself.

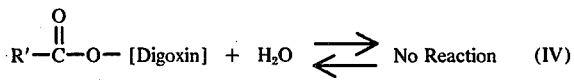

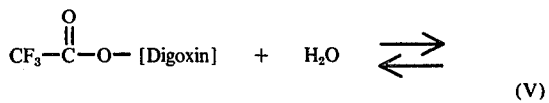

-continued

Thus, the addition of water simplifies the number of reaction products obtained and enables one to thereafter purify and isolate the desired product more readily. The amount of water should be enough so as to cleave off all the trifluoroacetic esters, but the exact amount is in no way critical to the present invention.

After the water addition step, the reaction mixture will contain the following: carboxylic acid esters of digoxin; unreacted digoxin; unreacted carboxylic acid; water; the inert, nonaqueous solvent medium; and the trifluoroacetic acid.

This next step is intended to purify the 15'- and 16'-esters of digoxin [formulae (1) and (2)] from the other constituents in the reaction mixture.

The preferred method is to dry the reaction mixture and then subject the dried reaction mixture to thin layer chromatography (TLC), although other chromatographic procedure (e.g. high pressure liquid chromatography) could be used. Such drying removes substantially all of the water and solvent, plus most of the trifluoroacetic acid.

After drying, the residue is dissolved in an organic solvent (e.g. ethanol or various mixture of methanol and chloroform) so it can be subjected to TLC. The TLC separates the desired 15- and 16-esters of digoxin from the unreacted digoxin, carboxylic acid and other undesired carboxylic acid esters of digoxin. For the reaction of digoxin with p-hydroxyphenylpropionic acid, solvent systems such as chloroform/methanol (7:1 by volume); hexanel/acetone/acetic acid (130:66:4 by volume) can be employed in the TLC. For the corresponding reaction involving imidazoleacetic acid, a solvent system such as chloroform/methanol (3:1 by volume) is commonly used.

It should be noted that only the 16'-carboxylic ester on digoxin need be formed; however, the 15'- and the 16'- are adjacent to each other on the terminal digitose and isomerization may occur during purification (i.e., ester group migrates from one of the neighboring hydroxyl groups to the other). Thus, there could be a mixture of 15'- and 16'-esters even though the reaction conditions are such that the 16'-ester was the only one originally formed. Both the 15'- and the 16'-esters of each respective acid possess identical affinities for the antibody. Therefore, since the mixture of 15'- and 16'-esters of the same acid are as effective as each individual purified ester, the complexity of the purification of the reaction products for the present invention is greatly reduced.

The purified mixture of 15'- and 16'-carboxylic esters of digoxin is then radio-labeled. It is preferred that $^{125}I$ be used as the radio-isotope. The radio-isotopes of iodine have the advantage of a higher specific activity over that which can be found with either tritium or carbon 14. The purified esters can be radio-labeled with $Na^{125}I$ according to the method of Greenwood and Hunter [see Hunter, W. M. and Greenwood, F. C., Nature, 194 495 (1962)]. When the digoxin derivative is radio-labeled with $Na^{125}I$, mono-iodinated and di-iodinated species are formed with other various labeled products. The monoiodinated product is separated from the unreacted $Na^{125}I$, di-iodinated digoxin species, various labeled by-products, and the unreacted starting material by TLC.

After the TLC, the thin layer plate upon which above products are separated into individual bands is removed from the solvent tank and air dried, then the individual radioactive bands are visualized by radioautography. The radioactive bnad corresponding to the mono-labeled $^{125}I$ digoxin derivative is carefully removed from the plate and the gel is extracted with 95% ethanol or other suitable solvent. Thus a solvent solution containing the $^{125}I$ digoxin derivative with maximum specific activity is obtained.

The high specific activity of $^{125}I$ enables one to use small sample volumes and relatively short counting times during the RIA of digoxin which results in greater precision and sensitivity. However, the present invention means to include all types of radio-labeling and all radio isotopes.

The radio-labeled reagents of this invention are suitable for use in RIA analysis procedures. Such procedures are well known in the art (see Skelley et al., supra) and will not be described in detail here. In general, such procedures for digoxin include a competitive analysis of the natural digoxin with an $^{125}I$-labeled digoxin derivative for a specific antibody. The amount of bound digoxin is separated from the free hapten and measured by a number of procedures. Although we favor the double antibody method, other standard methods include the use of dextran-coated charcoal, saturated ammonium sulfate, and polyethylene glycol precipitation. Commercial kits are now available for some of these RIA analysis methods.

While the instant invention has been primarily directed toward making reagents for use in RIA analyses, said reagents can be used in other competitive-binding protein assays.

The following specific embodiment of the present invention are shown to further describe the invention in more complete terms.

EXPERIMENT 1

Step 1: To 8 mg. (.05 millimoles) of imidazoeacetic acid in a microconical Teflon-capped reaction tube was added 40 microliters (0.266 millimoles) of trifluoroacetic anhydride. The mixture was heated at 40' C for 15 minutes during which time the carboxylic acid dissolved into the trifluoroacetic anhydride. Then 25 mg. (.03 millimoles) of digoxin in 1 milliliter of dry pyridine were added, and the mixture was heated for an additional 20 minutes at 40°–45° C.

Step 2: The temperature was allowed to reach room temperatures and 2 milliliters of $H_2O$ was added with stirring continued for an additional 10 minutes.

Step 3: The total mixture was then taken to dryness under reduced pressure and the residue tritiated with 8 milliliters of 95% ethanol. The 95% ethanol soluble products were analyzed by thin layer chromatography in a chloroform methanol mix (3:1 by volume).

This one thin layer chromatography system was capable of separating both the unreacted digoxin and the unreacted imidazoleacetic acid from the reaction products. An additional TLC in the above mentioned solvent system separated a mixture of the 15'- and 16'-esters from the other reaction products.

Step 4: The mixture of 15'- and 16'-imidazoleacetic acid esters of digoxin was then labeled $Na^{125}I$ by the Greenwood Hunter method.

This labeled mixture of esters possessed a high affinity for antisera and yielded a very low nonspecific binding affinity for proteins in serum or plasma and the surfaces of test tubes.

EXPERIMENT 2

Step 1: To 50 mg. digoxin (.064 millimoles) dissolved in 4 ml. dry pyridine were added 50 mg. p-hydroxyphenylpropionic acid (.32 millimoles) and 80 ml. of trifluoroacetic anhydride (0.532millimoles). The reaction was stirred for 40 minutes at 50°–55° C.

Step 2: The temperature of the reaction mixture was allowed to go to room temperature and 4 ml. of $H_2O$ was added. The mixture was stirred for 10 minutes.

Step 3: The entire reaction mixture was taken to dryness in vacuum to remove pyridine, water and trifluoroacetic acid. The residue was dissolved in a chloroform and methanol mixture (7:1 by volume). Unreacted digoxin, as well as the reaction products, were separated from the p-hydroxyphenylpropionic acid by a thin TLC [hexane-acetone-acetic acid (130:66:4 by volume)]. A further purification by TLC [chloroform to methanol (7:1 by volume)]was required to separate the unreacted digoxin from various esterified derivatives. The desired 15'- and 16'-esters were then removed from the other ester derivatives and unreacted digoxin.

Step 4: These 15'- and 16'-esters were then radiolabeled with $Na^{125}I$ by the Greenwood-Hunter method as in Example 1.

The labeled reagents possessed moderately high affinity for antisera. However, the nonspecific binding to the surfaces of vials in assays performed in polystyrene or polypropylene vials was high. In glass tubes, the background counts were reduced and the material easily performed in the radioimmunoassay of digoxin.

The terms and expressions which have been employed in the foregoing Abstract and Specification are used herein as terms of description and not of limitation, and there is no intention in the use of such terms or expressions, of excluding equivalents apt for use instead of subject techniques as shown and described, or portions thereof, it being recognized that the scope of the subject invention is to be understood as defined and limited solely by the claims which follow.

What is claimed is:

1. A radioimmunoassy reagent having the structural formulae:

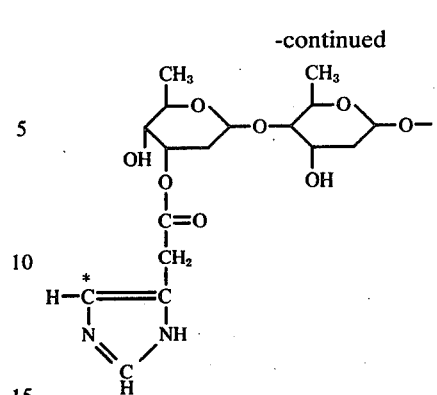

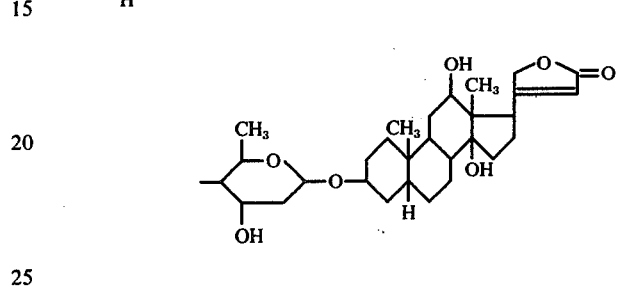

wherein the asterisk * indicates radioactive labelling.

2. The radioimmunoassay reagent of claim 1 wherein the radioactive labelling is with $^{125}I$.

3. In a method for the determined of quantities digoxin in blood by radioimmunoassay, the improvement comprising the use of a compound having the following formulae as the radioimmunoassay reagent:

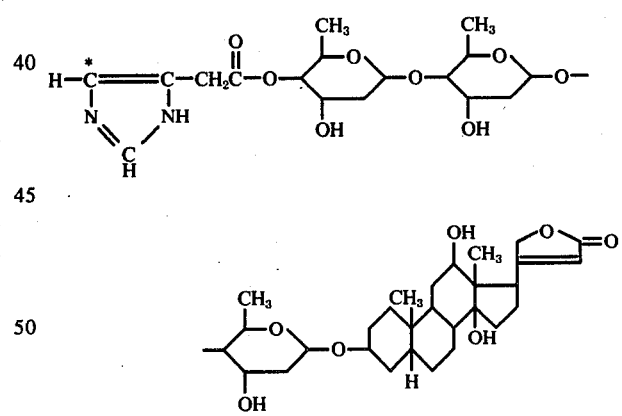

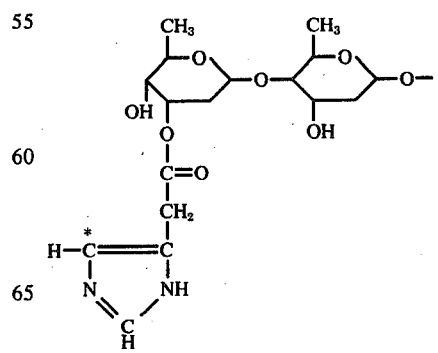

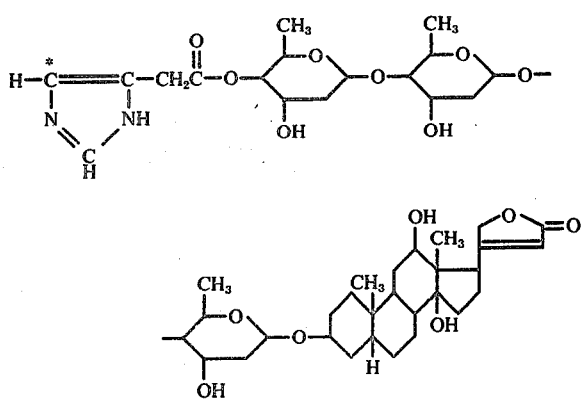

-continued

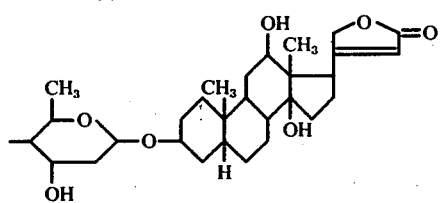

wherein the asterisk* indicates radioactive labelling.

4. The method of claim 3 wherein the radioimmunoassay reagent is radioactively labelled with $^{125}I$.

5. A radioimmunoassay reagent having the structural formulae:

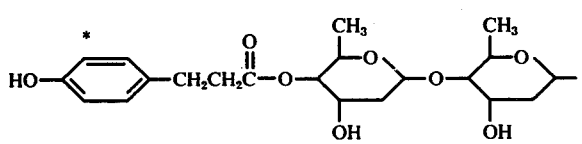

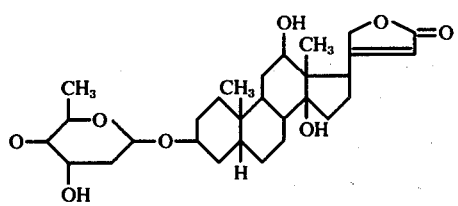

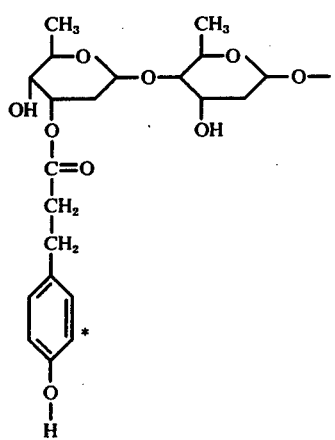

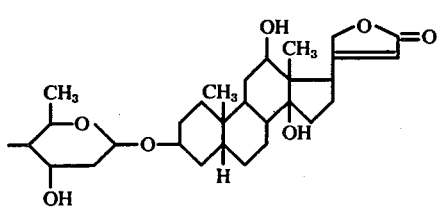

wherein the asterisk * indicates radioactive labelling

6. The radioimmunoassay reagent of claim 5 wherein the radioactive labelling is with $^{125}I$.

7. In a method for the determination of quantities of digoxin in blood by radioimmunoassay, the improvement comprising the use of a compound having the following formulae as the radioimmunoassay reagent:

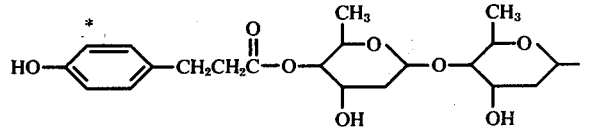

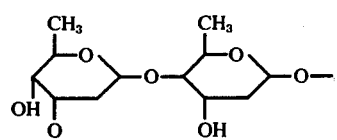

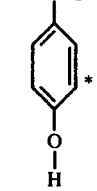

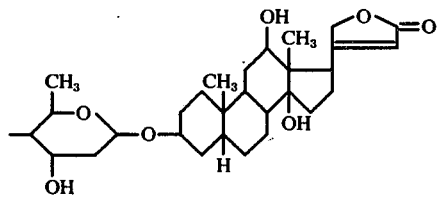

wherein the asterisk * indicates radioactive labelling.

8. The method of claim 7 wherein the radioimmunoassay reagent is radioactively labelled with $^{125}I$.

9. The method of making a radioimmunoassay or other competitive-protein assays derivative reagent for digoxin comprising the steps of:

a. reacting a carboxylic acid in the presence of trifluoroacetic anhydride with a solution of digoxin in an inert, nonaqueous solvent medium;

b. then mixing sufficient water into the reaction mixture so as to form derivatives having the following structural formulae:

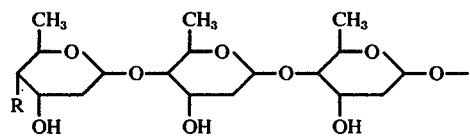

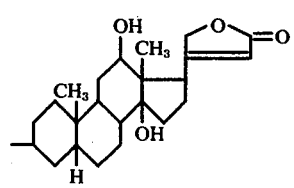

-continued
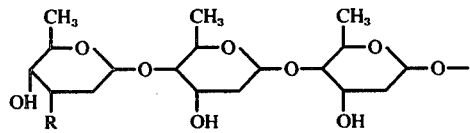
-continued
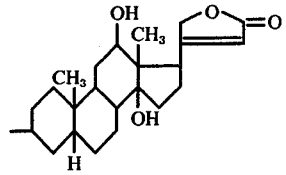
wherein R is an ester of imidazoleacetic acid or p-hydroxyphenylpropionic acid;
  c. purifying said derivatives from the other constituents of said reaction mixture; and
  d. tagging the derivatives with a radio-isotope so as to radio-label the derivative for use in the radioimmunoassay of digoxin.
* * * * *

UNITED STATES PATENT OFFICE
CERTIFICATE OF CORRECTION

Patent No. 4,021,535                 Dated May 3, 1977

Inventor(s) Alan J. Polito

It is certified that error appears in the above-identified patent and that said Letters Patent are hereby corrected as shown below:

Col. 1, Line 43 - "Skelly" should be --Skelley--

Col. 1, Line 68 - "(1973]." should be --(1973)].--

Col. 4, Line 35 - "acylation" should be --acetylation--

Col. 4, Line 47 - After "then", insert --the--

Col. 4, Line 52 - After "order", insert --of--

Col. 5, Line 21 - "there of" should be --thereof--

Col. 6, Line 14 - "nonaqueo us" should be --nonaqueous--

Col. 6, Line 18 - "given" should be --give--

Col. 6, Line 32 - "dixoane" should be --dioxane--

Col. 7, Line 67 - "monoiodinated" should be --mono-iodinated--

Col. 8, Line 7 - "bnad" should be --band--

Col. 8, Line 37 - "embodiment" should be --embodiments--

Col. 8, Line 43 - "imidazoeacetic" should be --imidazoleacetic--

Col. 8, Line 45 - "40" should be --40°C--

Col. 9, Line 28 - After "and", insert --the--

Col. 9, Line 50 - "radioimmunoassy" should be --radioimmunoassay-

Col. 10, Line 31 - "determined" should be --determination--

UNITED STATES PATENT OFFICE
CERTIFICATE OF CORRECTION

Patent No. 4,021,535   Dated May 3, 1977

Inventor(s) Alan J. Polito

It is certified that error appears in the above-identified patent and that said Letters Patent are hereby corrected as shown below:

Col. 11, line 60 - After "labelling", insert --.--.

Signed and Sealed this

First Day of November 1977

[SEAL]

Attest:

RUTH C. MASON
Attesting Officer

LUTRELLE F. PARKER
Acting Commissioner of Patents and Trademarks